United States Patent
Grelier et al.

(10) Patent No.: US 10,059,731 B2
(45) Date of Patent: Aug. 28, 2018

(54) PROCESS FOR DEPOLYMERIZATION OF LIGNIN BY LACCASES

(71) Applicants: INSTITUT POLYTECHNIQUE DE BORDEAUX, Talence (FR); UNIVERSITÉ DE BORDEAUX, Bordeaux (FR); Centre national de la recherche scientifique, Paris (FR)

(72) Inventors: Stéphane Grelier, Parentis en Born (FR); Georges Koumba Yoya, Bordeaux (FR)

(73) Assignees: Institut Polytechnique de Bordeaux, Talence (FR); Université de Bordeaux, Bordeaux (FR); Centre national de la recherche scientifique, Paris (FR)

( * ) Notice: Subject to any disclaimer, the term of this patent is extended or adjusted under 35 U.S.C. 154(b) by 0 days.

(21) Appl. No.: 15/039,796

(22) PCT Filed: Nov. 26, 2014

(86) PCT No.: PCT/EP2014/075680
§ 371 (c)(1),
(2) Date: May 26, 2016

(87) PCT Pub. No.: WO2015/078920
PCT Pub. Date: Jun. 4, 2015

(65) Prior Publication Data
US 2016/0376300 A1    Dec. 29, 2016

(30) Foreign Application Priority Data
Nov. 27, 2013 (FR) ...................................... 13 61718

(51) Int. Cl.
| | |
|---|---|
| *C07G 1/00* | (2011.01) |
| *C12P 7/22* | (2006.01) |
| *C12P 7/24* | (2006.01) |
| *C12P 7/40* | (2006.01) |
| *C12N 9/02* | (2006.01) |

(52) U.S. Cl.
CPC ............. *C07G 1/00* (2013.01); *C12N 9/0061* (2013.01); *C12P 7/22* (2013.01); *C12P 7/40* (2013.01); *C12Y 110/03002* (2013.01)

(58) Field of Classification Search
None
See application file for complete search history.

(56) References Cited

U.S. PATENT DOCUMENTS 4,453,004 A * 6/1984 Nelson ................... C07C 45/71
562/473

FOREIGN PATENT DOCUMENTS

WO    WO 2013/090430 A1    6/2013
WO    WO 2015/078920 A1    6/2015

OTHER PUBLICATIONS

Li et al., "Comparison of Fungal Laccases and Redox Mediators in Oxidation of a Nonphenolic Lignin Model Compound", Applied and Environmental Microbiology 1999, vol. 65, pp. 2654-2660.*
Arias et al., "Kraft Pulp Biobleaching and Mediated Oxidation of a Nonphenolic Substrate by Laccase from *Streptomyces cyaneus* CECT 3335", Applied and Environmental Microbiology 2003, vol. 69, pp. 1953-1958.*
Bourbonnais R. et al., "Lignin oxidation by Laccase Isozymes from Trametes versicolor and Role of the Mediator 2,2'-Azinobis(3-Ethylbenzthiazoline-6-sulfonate) in Kraft Lignin Depolymerization", Applied and Environmental Microbiology, American Society for Microbiology, US, vol. 61, No. 5, May 1, 1995, pp. 1876-1880.
Srebotnik, E. et al., "Degradation of nonphenolic lignin by the laccase/1-hydroxybenzotriazole system", Journal of Biotechnology, Elsevier Science Publishers, Amsterdam, NL, vol. 81, No. 2-3, Aug. 25, 2000, pp. 179-188.
French Search Report dated Oct. 24, 2014 for French Patent Application No. FR 13 61718 filed Nov. 27, 2013.
International Search Report dated Jan. 13, 2015 for International Patent Application No. PCT/EP2014/075680 filed Nov. 26, 2014.
Lu, Lin, "High-Valve Chemicals from Lignocellulosic Biomass," Progress in Chemistry, Aug. 2007, vol. 19, No. 7/8; pp. 1206-1216.
Shushui, Yang, China Light Industry Press, Jan. 2001; pp. 85-87.
Yan, Li, Guangdong Science & Technology Press, 2001; pp. 189-190.
Laisu, Xie, Chemical Industry Press, 2003; pp. 81-83.

* cited by examiner

*Primary Examiner* — Michelle F. Paguio Frising
(74) *Attorney, Agent, or Firm* — Knobbe, Martens, Olson & Bear, LLP

(57) ABSTRACT

A method for depolymerization of lignin includes oxidizing non-phenolic lignin by putting into presence, in at least one solvent, non-phenolic lignin, laccase, redox mediator and a source of oxygen, whereby a mixture including oxidized non-phenolic lignin is obtained, and further includes depolymerization of the oxidized non-phenolic lignin thereby obtained, by adding an oxidizer. The non-phenolic lignin is obtained from phenolic lignin by functionalization of phenol functions of the phenolic lignin.

9 Claims, No Drawings

PROCESS FOR DEPOLYMERIZATION OF LIGNIN BY LACCASES

This application is the U.S. National Phase under 35 U.S.C. § 371 of International Application No. PCT/EP2014/075680, filed Nov. 26, 2014, designating the U.S., and published in French as WO 2015/078920 on Jun. 4, 2015, which claims priority to French Patent Application No. 1361718, filed Nov. 27, 2013, the entire contents of which are incorporated herein by reference.

BACKGROUND OF THE INVENTION (1) Field of the invention

The present invention relates to a method for depolymerization of lignin.

Lignin is the second renewable most abundant biopolymer, after cellulose, and they both make up more than 70% of the total biomass.

Valorization of lignin therefore represents a major issue.

(2) Description of Related Art

In the paper-making industry, large amounts of lignin are obtained as byproducts or wastes, for which only a tiny portion is valorized in chemical form. In the sugar industry, large amounts of lignin are also obtained as wastes during extraction of the juice from sugarcane. The lignin is mainly used as a binder or dispersant, or for preparing biogas by a high temperature treatment (800° C.-1,000° C.). There also exist methods for depolymerization of lignin which involve chlorinated derivatives, unsatisfactory from an environmental point of view.

At the present time, there are few economically viable methods using lignin as a raw material for producing chemical compounds.

Therefore there exists a need for a novel method for valorization of lignin, which is economically viable and acceptable from an environmental point of view.

BRIEF SUMMARY OF THE INVENTION

The object of the present invention is to propose a novel method for depolymerization of lignin which is efficient and suitable from an environmental point of view, giving the possibility of accessing upgradable depolymerization products in various industrial fields, such as biorefineries, agri-feed industry or further cosmetics.

Another object of the present invention is to propose a method giving the possibility of accessing in a controlled way, to depolymerization products of diverse sizes such as 3,4-dimethoxybenzoic acid (methylated vanillic acid), veratraldehyde (methylated vanillin), veratrole (methylated guaiacol), or methylated diformyl guaiacol.

The method of the present invention proposes the combination, in a sequential way, of the action of an enzyme and the action of an oxidizer.

More particularly, the present invention relates to a method for depolymerization of lignin comprising:
  a step for oxidizing non-phenolic lignin by putting in presence in at least one solvent, non-phenolic lignin, a laccase, a redox mediator and a source of oxygen, whereby a mixture is obtained comprising oxidized non-phenolic lignin, and
  a step for depolymerization of the thereby obtained oxidized non-phenolic lignin, by adding an oxidizer,
said non-phenolic lignin being obtained from phenolic lignin by functionalization of phenol functions of said phenolic lignin.

DETAILED DESCRIPTION OF THE INVENTION

The method of the invention is non-microbiological, in the sense that no microorganisms (such as fungi) are used, endogenously expressing laccases.

The inventors surprisingly observed that the action on non-phenolic lignin of a laccase in the presence of a redox mediator and of an oxygen source, followed by the addition of an oxidizer, has the effect of efficiently depolymerizing the structure of lignin.

During the first step of the method (oxidation step), the hydroxyl functions in the benzyl position of the non-phenolic lignin are oxidized into ketone functions. During this step, the polymeric structure of lignin is not fragmented and substantially no C—C bond is cut.

During the second step of the method (a depolymerization step, also called fragmentation step), C—C bonds of the polymeric structure of lignin are broken. Without intending to be bound to a particular theory, the thereby broken C—C bonds are those which are found in the vicinity of the ketone functions formed during the first step of the method.

The method of the invention may be illustrated by the following illustrative scheme:

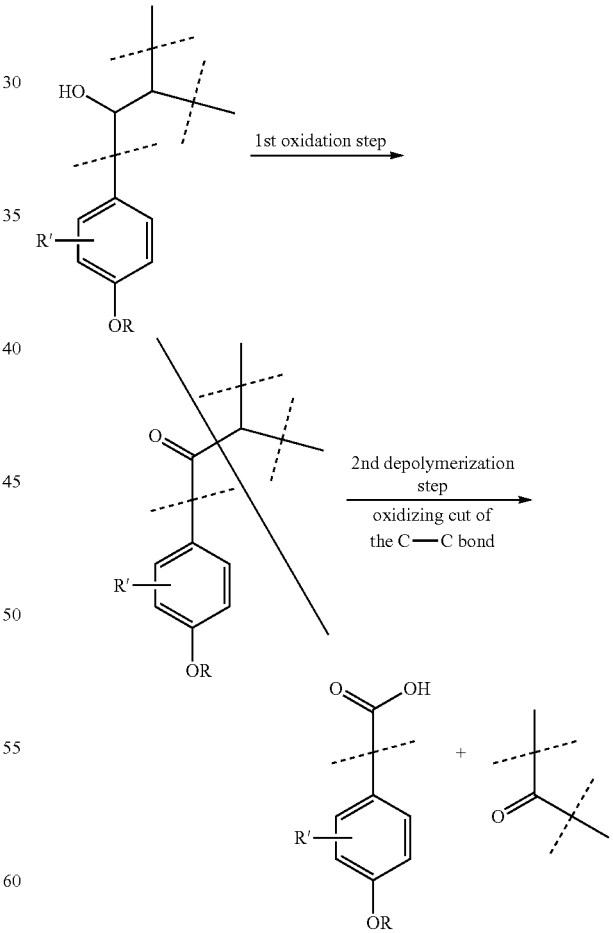

wherein the group —OR represents a functionalized phenol function of non-phenolic lignin and the group —R' represents an optional other substituent (different from a phenol function) of the illustrated phenyl group. The presence, the number and the type of group —R' depend on the lignin used. This may be for example one or several methoxy groups.

The scheme above is purely illustrative and only schematically reflects the structure of lignin.

As this will be discussed further on, both steps of the method are advantageously carried out subsequently to each other, in the same reactor.

The reaction conditions of the steps of the method of the invention will be described further on.

Generally, within the scope of the present application, by «reaction medium» is meant the medium in which take place the steps of the method and which comprises a lignin derivative, a laccase, a redox mediator, an oxygen source, at least one solvent, and optionally an oxidizer (depending on whether it has already been added or not).

By «putting them into presence», is thus meant the addition of a reagent in the reaction medium.

Said reaction medium may also comprise other reagents as they are described in the present application.

The raw material applied in the method, i.e. non-phenolic lignin, will now be described.

Non-phenolic Lignin

By «non-phenolic lignin», is meant a phenolic lignin derivative which is the reaction product of the functionalization of phenol functions (Ph-OH) of a phenolic lignin (also simply called «lignin»).

A non-phenolic lignin is a modified or functionalized lignin, in which at least one phenol function is modified. Preferably, at least 50%, or even at least 60%, or even at least 70%, or even at least 80%, or even at least 90%, or even at least 95%, or even at least 99% of the phenol functions of the lignin are modified.

A type of non-phenolic lignin is notably described in Srebotnik et al. (Journal of Biotechnology 81 (2000), 179-188).

Preferably, the non-phenolic lignin does not include any free phenol function (non-functionalized).

A non-phenolic lignin is obtained by reaction of a phenolic lignin with a functionalization agent able to convert phenol functions of said phenolic lignin into non-reactive functions during the oxidation step of the method. The functionalization of the lignin has the purpose of protecting the phenol functions during the oxidation step of the method and of preventing them from reacting. The functionalized phenol functions of the non-phenolic lignin are thus not reactive during the oxidation step by laccases.

Within the scope of the present invention, by «functionalization of the lignin» is meant the selective functionalization of the phenol functions, i.e. that the other hydroxyl functions of lignin (aliphatic alcohols in particular) are not functionalized. Preferably, functionalization is complete, i.e. all the phenol functions are functionalized.

The inventors have discovered that by using a phenolic lignin according to the method of the invention, the depolymerization of lignin is improved.

Alkylation is a functionalization example suitable for applying the method. For this and alkylation agent is used as a functionalization agent.

According to an embodiment, it is possible to use alkylated lignin as a non-phenolic lignin.

By «alkylated lignin», is meant the non-phenolic lignin in which the phenol functions are functionalized with alkyls (typically $C_1$-$C_{12}$ alkyls), for giving alkoxy functions.

Preferably, the alkylated lignin does not include any free phenol function, i.e. they are all (or almost all) in the form of alkoxy functions.

According to an advantageous embodiment, it is possible to use methylated lignin as a non-phenolic lignin.

For this a methylation agent is used as a functionalization agent.

By «methylated lignin», is meant alkylated lignin wherein the phenol functions are functionalized with methyls, in order to give methoxy functions.

Preferably, the methylated lignin does not include any free phenol function, i.e. they are all (or almost all) in the form of methoxy functions.

After functionalization of a phenolic lignin, in order to control the functionalization level and the functionalization selectivity, it is possible to quantify by $^{31}$P NMR the amount of possibly remaining phenolic functions (which would not have been functionalized). A method is notably described in Granat et al. J. Agric. Food Chem., 1995, 43(6), 1538-1544.

According to an embodiment, the non-phenolic lignin is an alkylated lignin which is obtained by putting into presence, in a basic aqueous solution, phenolic lignin and an alkylating agent.

Within the scope of the present invention, an alkylating agent is a compound capable of functionalizing the phenol functions with alkyl groups, by substituting the hydrogen atoms of said phenol functions with alkyl groups (in order to give alkoxy functions).

Preferably, an alkylating agent giving the possibility of selectively alkylating the phenol functions of lignin is used, i.e. the other hydroxyl functions of lignin (in particular secondary alcohols) are not alkylated into alkoxy functions.

Preferably, an alkylating agent is used, giving the possibility of completely alkylating the phenol functions of lignin, i.e. all (or almost all) phenol functions of lignin are alkylated into alkoxy functions.

According to an advantageous embodiment, the non-phenolic lignin is methylated lignin, which is preferably obtained by putting in presence in a basic aqueous solution lignin and a methylating agent.

Within the scope of the present invention, a methylating agent is a compound capable of functionalizing the phenol functions with methyl groups, by substituting the hydrogen atoms of said phenol functions with methyl groups.

Preferably, a methylating agent is used, giving the possibility of selectively methylating the phenol functions of lignin, i.e. the other hydroxyl functions of lignin (in particular secondary alcohols) are not methylated into methoxy functions.

The putting into presence of the methylating agent is typically carried out drop wise.

The putting into presence is typically followed by a step for heating the reaction medium, to a temperature typically comprised from 50° C. to 100° C.

As a methylating agent, mention may be made of dimethylsulfate (or dimethyl sulfate), dimethyl carbonate (DMC), methyl iodide and diazomethane.

Preferably, dimethylsulfate is used, which allows complete and selective methylation of the phenol functions of a phenolic lignin.

The step for methylation of lignin may typically be carried out according to a method described in Sadeghifar et al. Ind. Eng. Chem. Res. 2012, 51, 16713-16720.

The lignin is dissolved in a basic aqueous solution, typically soda (for example at 0.7 M). The obtained mixture is stirred, typically at room temperature and a methylating agent is added, preferably drop wise (in an amount of about 50 equivalents of methylating agent based on the number of equivalents of phenol functions). The mixture is typically heated (for example to 80° C.) until the reagents are consumed. The mixture is then acidified, filtered and the obtained solid is washed with distilled water and dried for providing the methylated lignin.

Without intended to be bound to a particular theory, the inventors observe that methylation of lignin, by selectively and completely blocking the phenol functions, gives the possibility of avoiding in a very efficient way the polymerization reactions of lignin during the action of laccase, and thus improving depolymerization.

The effect of methylation is notably illustrated in the comparative examples described hereafter. A (non-methylated) non-phenolic lignin treated by the method of the invention is not depolymerized.

Phenolic Lignin

Within the scope of the present invention, by «phenolic lignin» or «lignin», is meant a natural form of lignin, including free phenol functions (Ph-OH).

The structure of lignin appears as a complex three-dimensional lattice, from the polymerization of base units which have as a backbone a phenylpropane unit. Lignin therefore more generally designates lignin(s), depending on the base units which make it up. From among the base units of lignin, also called monolignols, mention may mainly be made of paracumarylic alcohol, coniferylic alcohol and sinapylic alcohol.

Within the scope of the present invention, by "depolymerization" is meant a reaction during which the covalent bonds of the polymeric structure of lignin are broken, leading to depolymerization products of a size smaller than the initial lignin.

By «smaller size», is meant that the depolymerization products obtained according to the method of the invention have a molecular mass smaller than that of the initial non-phenolic lignin.

However, within the scope of the present invention, the meaning of the term «depolymerization» should not be limited to the transformation of the non-phenolic lignin into base units as described above.

Typically, the depolymerization products of lignin obtained according to the method of the invention are formed with a base unit, with a few base units, or even with a few tens of base units. Generally mixtures of depolymerization products are obtained, including a different number of base units.

Generally, given the complex structure of lignin, the method of the invention provides a mixture of depolymerization products with diverse sizes and structures, which may bear various functional groups, such as ketone, aldehyde, acid, phenol, alcohol or methoxy groups for example, preferably acid, methoxy, alcohol and ketone groups.

Said depolymerization products may be defined as «monomers», «oligomers» or «fragments» of non-phenolic lignin.

Thus, by a «depolymerization method», is also meant a «fragmentation method» of the structure of lignin.

The depolymerization products obtained according to the method of the invention have a size comprised between 100 g/mol and 5,000 g/mol, preferably between 150 g/mol and 4,000 g/mol, advantageously between 200 g/mol to 3,000 g/mol, preferentially between 500 g/mol and 2,500 g/mol.

The mixture of depolymerization products of lignin is typically characterized by its average molecular mass $M_w$, which represents the average of the molar masses weighted by the mass of each product, and which has the formula:

$$M_w = \frac{\sum_i n_i M_i^2}{\sum_i n_i M_i}$$

wherein $n_i$ designates the number of products i and $M_i$ designates the molecular mass of the product i.

For a mixture of depolymerization products obtained according to the method of the invention, the average molecular mass, $M_w$, may be measured by steric exclusion chromatography (SEC for "Size Exclusion Chromatography").

The mixture of depolymerization products typically has an average molecular mass $M_w$ comprised between 100 g/mol and 5,000 g/mol, preferably between 150 g/mol and 4,000 g/mol, advantageously between 200 g/mol to 3,000 g/mol, preferentially between 500 g/mol and 2,500 g/mol.

The mixture of depolymerization products obtained according to the method of the invention may also be characterized by the molar ratio between the mass average molecular mass $M_w$ of said mixture and the mass average molecular mass of the initial lignin $M_{lig}$.

Typically, by using the method of the invention, a molar ratio $M_w/M_{lig}$ comprised between ⅓ and 1/10 is obtained.

The non-phenolic lignin being used as a raw material in the method of the invention may be obtained by any functionalization method (alkylation, methylation, . . . ) known per se, from any available source of phenolic lignin, whether this is a commercial source or else extracted from industrial residues rich in lignin.

As a source of phenolic lignin, it is possible to use the lignins described below, and preferably Kraft lignin (for example stemming from the black liquor), optionally purified, or else the lignin of cane sugar bagasse, or any other industrial lignin.

The lignins which may be used within the scope of the present invention are notably described in Lignins and Lignans: Advances in Chemistry, Cyril Heitne, John Schmidt, CRC Press, Taylor&Francis Group, 2010.

Advantageously, the lignin has been subject to a pretreatment so as to make it soluble in an aqueous medium.

As a phenolic lignin, it is possible to use Kraft lignin, for example extracted from a black liquor.

Kraft lignins (also called thiolignins) are water-soluble compounds stemming from the industrial production of paper pulp by using sulfate ions.

Kraft lignin which may be used in the method of the invention is typically obtained by extraction of black liquor, which is the baking liquor stemming from the manufacturing of craft paper. This is an aqueous solution consisting of residues of lignin and dissolved hemicellulose from paper pulp, as well as other inorganic chemical compounds (dissolved salts).

The purification of the black liquor is typically carried out as follows. The black liquor is acidified in order to cause precipitation of lignin. The obtained solid is centrifuged, isolated and extracted with ethanol. The liquid fractions are recovered and concentrated by evaporating the ethanol. The residue is washed with an acid solution for removing the residual salts. Kraft lignin is thereby obtained.

Kraft lignin extracted from black liquor may further be purified as follows for removing the impurities (typically monophenol compounds and degradation residues). Kraft lignin is put into presence with tetrahydrofurane, the obtained mixture is filtered for removing the solid, the filtrate is concentrated by evaporating the solvent, and then the obtained solid is washed with diethyl ether in order to remove organic impurities, such as monophenol compounds (vanillin, vanillic acid, . . . ) and degradation residues. The recovered solid is dried in order to obtained purified Kraft lignin.

As a phenolic lignin, it is also possible to use lignin stemming from sugarcane bagasse.

Sugarcane bagasse is the fibrous residue of sugarcane obtained after extracting the juice. It forms a significant waste of the sugar industry, which is not sufficiently valorized. Sugarcane bagasse lignin is commercially available (Solvay).

It is also possible to use a source of industrial lignin or else mixtures of compounds comprising lignins, typically biomass mixtures comprising lignin and other constituents, such as of cellulose and/or hemicellulose, or further a mixture of Kraft lignins.

The lignin used in the method of the invention typically has a mass average molecular mass ($M_{lig}$) comprised between 1,000 and 10,000 g/mol, preferably between 1,000 and 5,000 g/mol.

The mass average molecular mass of the initial lignin ($M_{lig}$) represents the mass of the molar masses weighted by the mass of each size of lignin, and has the formula:

$$M_{lig} = \frac{\sum_j n_j M_j^2}{\sum_j n_j M_j}$$

wherein $n_j$ designates the number of lignin molecules of size j and $M_j$ designates the molecular mass of a lignin of size j.

This value is generally indicated by the lignin provider or else may be determined by the size exclusion chromatography measurement, as described above.

The steps of the method of the invention will now be described.

Oxidation Step by Laccases

The first step of the method of the invention consist of putting into presence, in at least one solvent, non-phenolic lignin as described above, a laccase, au redox mediator and an oxygen source.

This step leads to the oxidation of the non-phenolic lignin by the action of the laccase/mediator system in the presence of an oxygen source, whereby a mixture is obtained comprising oxidized non-phenolic lignin.

By «oxidized non-phenolic lignin», is meant a non-phenolic lignin as defined above, wherein the hydroxyl functions in the benzyl position have been selectively converted into ketone functions.

During this step, the non-phenolic lignin is essentially not depolymerized, i.e. this step does not affect (or only very little) the polymeric structure of lignin, in particular it does not break (or only very slightly), C—C bonds.

Laccase

The laccases (EC 1.10.3.2) are a family of enzymes which are found in many plants, fungi and microorganisms.

In vivo, laccases have an oxidizing activity and act as a catalyst within an enzymatic oxidation process.

The laccases which may be used in the method of the invention may be derived from plants, from fungi or microorganisms. The laccases stemming from fungi notably include the laccases of the *Aspergillus*, *Neurospora* (for example *Crassa Neurospora*), *Podospora*, *Botrytis*, *Collybia*, *Fomes*, *Lentinus*, *Pleurotus*, *Trametes* (for example *Trametes villosa* and *Trametes versicolor*), *Rhizoctonia* (for example *Rhizoctonia solani*), *Coprinus* (for example *Coprinus cinereus*, *Coprinus comatus*, *Coprinus friesii* and *Coprinus plicatilis*), *Psathyrella* (for example *Psathyrella condelleana*), *Panaeolus* (for example *Panaeolus papilionaceus*), *Myceliophthora* (for example *Myceliophthora thermophila*), *Schytalidium* (for example *Schytalidium thermophilum*), *Polyporus* (for example *Polyporus pinsitus*), *Phlebia* (for example *Radiata phlebia*), *Pycnoporus* (for example *Pycnoporus cinnabarinus*) or *Coriolus* (for example *Coriolus hirsutus*) genera. The laccases stemming from bacteria stem for example from *Bacillus*.

Preferably, a laccase stemming from *Trametes versicolor*, marketed by Sigma Aldrich is used.

The ratio of the amount of laccase put into presence (in mg) over the initial amount of non-phenolic lignin present in the reaction medium (in grams) is generally comprised between 0.1/1 and 5/1.

Within the scope of their use in vitro, for oxidation of a substrate consisting of voluminous molecules (typically with a molecular mass of more than 5,000 g/mol), the laccases are generally associated with a «redox mediator», which is a chemical compound of small size (typically with a molecular mass of less than 1,000 g/mol) acting as a redox intermediate between the molecules of laccases and the substrate molecules to be oxidized. Redox mediators are notably described in Bourbonnais R. Appl. Enviro. Microbiol. 1995, 61, 1876-1880.

The redox mediators are also designated as electron transfer agents since they facilitate electron transfer between the laccases and the substrate to be oxidized.

The principle of redox mediation is a technology known per se.

Within the scope of the treatment of lignin with laccases, in the absence of a redox mediator, the chemical interactions between the laccases, which are large size proteins, and the lignin molecules, which are polymers of great size, would be unfavored. Thus a redox mediator is added in order to accelerate the enzymatic oxidation process catalyzed by the laccases.

The ratio of the amount of redox mediator put into presence (in mmol) over the amount of laccase put into presence (in mg) is generally comprised between 1/1 and 1/50.

Preferably, the redox mediator applied according to the method of the invention is 2,2-azino-bis-(3-ethylbenzothiazoline-6-sulfonic acid) (ABTS).

This mediator is particularly adapted for the oxidation of lignin by laccases.

Unlike other redox mediators, such as hydroxybenzotriazole (HOBt) which rapidly degrades in the presence of a laccase by losing its mediation activity (HOBt becomes HBt by losing an oxygen atom), ABTS has better activity as a redox mediator.

The following redox mediators may also be suitable for applying the invention: violuric acid, hydroxyanthranilic acid, TEMPO, N-hydroxyphthalimide (Chakar et al. Can. J. Chem. 82: 344-352 (2004)).

Oxygen Source

By «oxygen source», is meant a reagent capable of regenerating (re-oxidizing) the active sites of the laccase involved within the scope of the enzymatic oxidation process mentioned above, which in fine provides the oxidized non-phenolic lignin from non-phenolic lignin. By «oxygen», is meant here dioxygen ($O_2$).

Preferably, the oxygen source is a gas comprising oxygen, such as air or pure oxygen.

As an oxygen source, mention may be made of pure oxygen ($O_2$), which is put into the presence, by bubbling at atmospheric pressure or under a pressure of a few bars, in the reaction medium comprising, at the beginning of the oxidation step, non-phenolic lignin, a laccase, a redox mediator and at least one solvent. In this way, one manages to advantageously saturate the reaction medium with dissolved oxygen.

As an oxygen source, it is possible to also mention air or any mixture of gases enriched with oxygen.

By «putting into the presence of an oxygen source», is meant the introduction of said oxygen source in the reaction medium of the method of the invention. Said putting into presence may be carried out in a one-off or prolonged way, preferably prolonged way, the sought goal being to saturate the reaction medium with dissolved oxygen.

Alternatively, it is possible to use instead of the oxygen source, any oxidizer capable of regenerating (re-oxidizing) the active sites of the laccase involved in the enzymatic oxidizing process described above.

The first step of the method is advantageously carried out under conditions of pH and temperature suitable for the reactivity of the laccase used, i.e. under conditions of pH and temperature which do not de-naturate the properties of the laccase.

Preferably, the first step of the method of the invention is carried out in an acid medium, typically in a buffer at pH=4.

Preferably, the first step of the method of the invention is carried out at a temperature comprised between 20° C. and 60° C., preferably around 40° C.

These conditions are particularly suitable for applying the laccase stemming from *Trametes versicolor*.

It is possible to adopt the optimum pH and temperature conditions associated with the type of laccase used, these conditions being generally known for a given laccase.

The first step of the method according to the invention is carried out in the presence of at least one solvent.

According to an embodiment, the solvent is a mixture comprising water and a polar organic solvent.

Preferably, the solvent is a mixture comprising a buffer solution with an acid pH (typically pH=4) and a polar organic solvent.

The use of such a mixture as a solvent has the advantage of solubilizing the non-phenolic lignin as well as the whole of the reagents put into presence. A homogenous reaction mixture is thereby obtained, in which chemical interactions are facilitated.

According to this embodiment, the solvent preferably comprises between 30% and 70% by volume of water, advantageously between 40% and 60%, based on the total volume of the solvent.

The solvent supplement typically consists of a polar organic solvent, preferably sufficiently volatile so as to be separated from the depolymerization products by evaporation, optionally under reduced pressure.

The solvent is typically a mixture of water for solubilizing the laccase and of an ether capable of solubilizing the non-phenolic lignin, such as dioxane. A dioxane/water (1/1) mixture may typically be used.

The first step is carried out according to a dilution such that for 1 g of non-phenolic lignin, a solvent volume is used comprised from 10 ml to 100 ml, preferably from 30 ml to 70 mL, typically 50 ml.

One skilled in the art will be able to adapt the dilution of the reaction medium depending on the solubility of the initial non-phenolic lignin, on the temperature of the reaction and/or on the viscosity of the reaction mixture.

Depolymerization Step

The inventors discovered that by putting into presence the oxidized non-phenolic lignin stemming from the first step of the method of the invention with an oxidizer, one manage to efficiently depolymerize the structure of lignin so as to obtain depolymerization products of lignin.

By "oxidizer", is meant a substance capable of oxidizing the species present in the reaction medium. Preferably, the oxidizer is nucleophilic.

As a nucleophilic oxidizer, mention may for example be made of peroxides, like hydrogen peroxide ($H_2O_2$) and benzoyl peroxide, or else compounds such as $O_3$, $KMnO_4$ and $NaIO_4$, or further any nucleophilic oxidizer conventionally used in organic chemistry.

The oxidizer is preferably hydrogen peroxide ($H_2O_2$).

The hydrogen peroxide is typically available as a 35% by mass aqueous solution, which is equivalent to a molar concentration of about 10 M.

Preferably, typically when the oxidizer is hydrogen peroxide, the ratio of the amount of oxidizer put into presence (in mols) over the amount of oxidized non-phenolic lignin present in the reaction medium (in grams) is comprised between 0.01/1 and 0.02/1.

The second step of the method preferably occurs in a basic medium, notably when the oxidizer is hydrogen peroxide. Thus, when the first step of the method takes place in a medium with neutral or acid pH, it is then necessary to pass to a basic medium, and this preferably before putting into presence the oxidizer. In order to pass into a basic medium, it is possible to use any method known per se, such as the addition of a basic aqueous solution, typically of soda, in the reaction medium.

Application of the Method

A typical application of the method of the invention will now be described.

The steps of the method are typically applied one after the other in the same reactor.

Alternatively, it is possible to carry out both of these steps in a separate way, in two distinct reactors.

According to a particular embodiment, in a reactor provided with a heating system, with a stirring means and optionally a cooling means, non-phenolic lignin and a portion of the solvent are introduced and stirred until full dissolution. A redox mediator solution is then added in one portion of the solvent, and then a laccase solution is added in the remainder of the solvent.

The oxygen source is then put into presence preferably continuously, typically by bubbling in the reaction medium when the oxygen source is a gas.

The temperature of the mixture is typically maintained between 20° C. and 60° C., preferably around 40° C., until complete oxidation of the non-phenolic lignin is attained. At this stage, the first step of the method is completed.

It is then possible to recover the oxidized non-phenolic lignin.

Alternatively, it is possible to advantageously continue the method by carrying out the second step in the same reactor. According to this embodiment, it is possible to be in a basic pH by basifying if required the reaction medium.

It is then possible to add the oxidizer, preferably continuously, typically drop wise, when the oxidizer is a solution.

The temperature of the mixture is typically maintained to be greater than 70° C., typically around 90° C.

The progression of the reaction is tracked by SEC (size exclusion chromatography).

The stirring and the heating of the reaction medium is continued until the desired depolymerization degree is obtained.

Once the depolymerization is completed, the depolymerization products of lignin may be recovered, by using standard purification techniques in the field, i.e. filtration, extraction, distillation and/or separation by chromatography. Notably, the solvent may be removed by evaporation, optionally under reduced pressure.

The method of the invention will now be illustrated by means of examples and comparative examples.

EXAMPLES

Reagents
Black liquor (provided by SMURFIT Kappa)
Dimethyl sulfate (marketed by Sigma Aldrich)
Sugarcane bagasse lignin (provided by SOLVAY)
2,2-azino-bis-(3-ethylbenzothiazoline-6-sulfonic acid) (ABTS) (marketed by Sigma Aldrich)
A laccase from *Trametes versicolor* (marketed by Sigma Aldrich)
Acetate buffer (pH=4; 50 mM)
Hydrogen peroxide (35%) (marketed by Sigma Aldrich)

Example 1

Extraction of Kraft Lignin from the Black Liquor

The Kraft lignin was extracted from the baking liquor (marketed by SMURFIT KAPPA) with an acid treatment, so as to cause its precipitation. A post-treatment with ethanol gives the possibility of removing the residual sodium salts.

800 g of black liquor are dissolved in 2 of distilled water and the mixture is slowly acidified (from pH=13 to pH=1.5) by means of a 6N HCl solution. The mixture is then centrifuged at 4,000 rpm for 10 minutes, the pellet is recovered and again treated with a HCl solution at pH=1.5 and again centrifuged (3 times treated with HCl at pH=1.3). Ethanol is then added to the obtained solid. After filtration, the ethanol phase is evaporated and the residue is washed with an HCl solution at pH=1.5 for removing the residual salts. After centrifugation, the pellet is recovered and freeze-dried. A 180 g of Kraft lignin are obtained.

From the 180 g of Kraft lignin which are thereby obtained, 10 g are sampled which are dissolved in 200 ml of tetrahydrofurane (THF). After stirring for 30 minutes with ultrasound, the mixture is filtered for removing the white solid deposit, insoluble in THF. After evaporation of the THF, 9.2 g of a brown solid are obtained. This brown solid is dissolved in 100 ml of diethyl ether ($Et_2O$). A fraction remains insoluble in $Et_2O$ (8.1 g) and the soluble fraction (0.9 g) is analyzed by GC-MS after silylation in order to make these compounds volatile.

This analysis demonstrates the presence of monophenols like vanillin or vanillic acid and residues from the degradation of the sugars. The insoluble fraction consists of purified Kraft lignin, which may be used subsequently for the methylation and the depolymerization method of the present invention.

Example 2A

Methylation of Kraft Lignin 1 g of Kraft lignin is dissolved in 20 ml of a 0.7 M NaOH solution (0.56 g) and the mixture is stirred at room temperature for 10 minutes, and then 0.8 mL of dimethylsulfate (($MeO)_2SO_2$) are slowly added (drop wise). Stirring is continued for 30 minutes at room temperature. The reaction mixture is then heated to 80° C. for 4 hours, while adding a 0.7 M NaOH solution for homogenizing the reaction medium (about 10 mL of additional 0.7 M NaOH are added). After 4 hours of reaction, the mixture is brought back to room temperature and acidified with a 2 M HCl solution down to a pH=2. The reaction crude is filtered and the obtained solid is washed with distilled water and then dried by freeze-drying. 0.874 g of methylated lignin are obtained.

Example 2B

Methylation of the Sugarcane Bagasse Lignin

The sugarcane bagasse lignin was provided by SOLVAY, was used without any preliminary pre-treatment.

The bagasse lignin is treated under the conditions described in Example 2A. 0.92 g of methylated lignin are obtained.

Example 3A

Depolymerization of Methylated Lignin (Derived from Kraft Lignin)

1 g of methylated lignin obtained in Example 2A is dissolved in 25 mL of dioxane and the mixture is stirred at room temperature until full dissolution.

Next, a solution of 51 mg of 2,2-azino-bis-(3-ethylbenzothiazoline-6-sulfonic acid) (ABTS) (0.1 mmol) in 1 ml of acetate buffer (pH=4; 50 mM) is prepared which is added to the methylated lignin solution.

Next, a solution of 5 mg of laccase in 200 mL of acetate buffer is then prepared, 24 ml of this solution are sampled which are slowly added to the medium containing the methylated lignin at 40° C. After adding the laccase, oxygen gas is introduced into the mixture by bubbling for 1 hour at 40° C., by using a flask filled with oxygen.

After 22 hours of reaction at 40° C., 1 mL of a 3 M NaOH solution is added, and then 1 mL of an aqueous solution of hydrogen peroxide (35%, 10 mmol) is slowly added, the mixture being stirred at 90° C.

The progression of the reaction is tracked by SEC (size exclusion chromatography). The analysis by SEC is conducted by using three columns of the TSK-gel type (3000 PW, 4000 PW, 3000 PW) coupled in series, with 1 M of sodium hydroxide until pH=12 and $NaN_3$ (3%) in osmosed water as an eluant. The flow rate is 1 mL/min and the detection is ensured by UV at a wavelength of 280 nm.

The first step of the reaction (action of the laccase/ABTS system) leads to low depolymerization. The second step (action of hydrogen peroxide) leads to strong depolymerization, with the formation of molecules of low molecular mass which were isolated and identified.

After 40 hours of reaction, the mixture is brought back to pH=6-7 by means of a 1 N HCl solution and the reaction crude is extracted with dichloromethane (3×50 ml). After drying the organic phase on sodium sulfate ($Na_2SO_4$) and evaporation of the volatile solvents, the crude is purified by flash chromatography (with as an eluant: dichloromethane/methanol 99/1 to 90/10).

30 mg of 3,4-dimethoxybenzoic acid were thus isolated from 1 g of methylated lignin obtained in Example 2A.

Comparative Example 1

As a comparison, the purified Kraft lignin obtained in Example 1 was subject to the action of the laccase/ABTS system, by directly applying the reaction conditions described in Example 3A (i.e. without carrying out methylation of the lignin).

The progression of the reaction is tracked by SEC (conditions described above):

| t (hours) | $M_p$ | $M_n$ | $M_w$ |
|---|---|---|---|
| 0 | 661 | 902 | 1326 |
| 2 | 842 | 1254 | 1662 |
| 73 | 905 | 1036 | 1821 |

$M_p$: molecular weight peak, in g/mol
$M_n$: number average molecular mass, in g/mol
$M_w$: mass average molecular mass, in g/mol It is observed that the average molecular mass of the species in presence increases with the duration of reaction.

Thus, when the action of the laccase/ABTS system is carried out on non-methylated Kraft lignin, no depolymerization is observed, but on the contrary an increase in the molecular mass of the lignin.

Example 3B

Depolymerization of Methylated Lignin (Derived from Bagasse Lignin)

The methylated lignin obtained in Example 2B is treated by applying the reaction conditions described in Example 3A (the action of the laccase is prolonged for 65 hours, after which hydrogen peroxide is added).

The progression of the reaction is tracked by SEC (conditions described above):

| t (hours) | $M_p$ | $M_n$ | $M_w$ |
|---|---|---|---|
| 0 | 5054 | 1414 | 10245 |
| 2 | 4806 | 759 | 8681 |
| 65 | 3555 | 269 | 6857 |
| 70 | 2443 | 1601 | 4907 |
| 80 | 1525 | 130 | 2112 |

The first step of the reaction (laccase/ABTS) leads to low depolymerization. The second step (addition of hydrogen peroxide at t=65 h) leads to depolymerization with the production of phenols of low molecular mass which were not isolated and identified.

Comparative Example 2

As a comparison, the bagasse lignin is subject to the action of the laccase/ABTS system, by directly applying the reaction conditions described in Example 3A (i.e. without carrying out methylation of lignin).

The progression of the reaction is tracked by SEC (conditions described above):

| t (hours) | $M_p$ | $M_n$ | $M_w$ |
|---|---|---|---|
| 0 | 2254 | 145 | 4957 |
| 1 | 4048 | 417 | 8245 |
| 24 | 9242 | 4282 | 17329 |

It is observed that the average molecular mass of the species in presence increases with the duration of reaction.

Thus, when the action of the laccase/ABTS system is carried out on non-methylated bagasse lignin, no depolymerization is observed, but on the contrary an increase in the molecular mass of the lignin.

Comparative Example 3

As a comparison, the methylated lignin obtained in Example 2B was subject to the action of hydrogen peroxide in a basic medium, without subjecting it to the action of the laccase/ABTS system beforehand.

1 g of methylated lignin obtained in Example 2B is dissolved in 25 mL of dioxane and the mixture is stirred at room temperature until full dissolution.

Next, 25 mL of osmosed water are added to the mixture.

1 mL of a 3 M NaOH solution is added, and then 1 ml of an aqueous solution of hydrogen peroxide (35%, 10 mmol) is slowly added, the mixture being stirred at 90° C.

The progression of the reaction is tracked by SEC (conditions described above):

| t (hours) | $M_p$ | $M_n$ | $M_w$ |
|---|---|---|---|
| 0 | 5054 | 1414 | 10245 |
| 5 | 2541 | 404 | 4651 |
| 15 | 2394 | 153 | 4725 |

A less significant depolymerization of the methylated lignin is observed than when it is treated beforehand with the action of the laccase/ABTS system.

Without intending to be bound to a particular theory, this partial depolymerization is explained by the fact that, in the lignin (and therefore in the methylated lignin), a certain percentage of hydroxyl functions intended to be oxidized by being put in the presence of the laccase/mediator system are already in an oxidized states, i.e. as ketones. The oxidizing rupture of the C—C bonds in the vicinity of these ketone functions causes partial depolymerization.

This example nevertheless shows that the first step of the method is required for optimizing the depolymerizing action of the hydrogen peroxide.

The comparative analysis of the bagasse lignins obtained at the end of Examples 2B, 3B and at the end of comparative Example 3 shows that the fragmentation of lignin is most efficient when the methylated lignin is successively subject to the action of the laccase/ABTS system and then to the action of hydrogen peroxide:

| | |
|---|---|
| Lignin of Example 2B, non-depolymerized | $M_{lig}$ = 10245 |
| Lignin of Example 3B, treated with laccase + $H_2O_2$ | $M_w$ = 2112 |
| Lignin of the comparative Example 3, treated with $H_2O_2$ | $M_w$ = 4725 |

What is claimed is:

1. A method for depolymerization of lignin, comprising:
    oxidizing a non-phenolic lignin by adding together the non-phenolic lignin, laccase, a redox mediator and an oxygen source in at least one solvent, thereby obtaining a mixture comprising oxidized lignin; and
    depolymerizing the oxidized lignin in the obtained mixture by adding an oxidizer,
    wherein said non-phenolic lignin is prepared by alkylation of phenol functional groups of a phenolic lignin.
2. The method according to claim 1 wherein the non-phenolic lignin is methylated lignin.

3. The method according to claim 2, wherein the methylated lignin is obtained by adding together the phenolic lignin and a methylation agent in a basic aqueous solution.

4. The method according to claim 3, wherein the methylation agent is dimethyl sulfate.

5. The method according to claim 1, wherein the oxygen source is pure oxygen or air.

6. The method according to claim 1, wherein the redox mediator is 2,2-azino-bis-(3-ethylbenzothiazoline-6-sulfonic acid).

7. The method according to claim 1, wherein the oxidizer is hydrogen peroxide.

8. The method according to claim 1, wherein the oxidizing is carried out in a basic medium.

9. The method according to claim 1, wherein the non-phenolic lignin stems from the alkylation of phenol functional groups of a Kraft lignin or sugarcane bagasse lignin.

\* \* \* \* \*